(12) United States Patent
Dardenne et al.

(10) Patent No.: US 7,309,690 B2
(45) Date of Patent: Dec. 18, 2007

(54) USE OF THYMULIN-LIKE PEPTIDES FOR MAKING PAIN-RELIEVING MEDICINES

(75) Inventors: Mireille Dardenne, Paris (FR); Jean-François Bach, Paris (FR); Bared Safieh-Garabedian, Beyrouth (LB); Jean-Marie Pleau, Palaiseau (FR); Nayef Saade, Beyrouth (LB)

(73) Assignees: Centre National de la Recherche Scientifique, Paris (FR); Institut National de la Sante et de la Recherche Medicale (INSERM), Paris (FR)

( * ) Notice: Subject to any disclaimer, the term of this patent is extended or adjusted under 35 U.S.C. 154(b) by 157 days.

(21) Appl. No.: 10/492,170

(22) PCT Filed: Oct. 8, 2002

(86) PCT No.: PCT/FR02/03428

§ 371 (c)(1),
(2), (4) Date: Nov. 22, 2004

(87) PCT Pub. No.: WO03/030927

PCT Pub. Date: Apr. 17, 2003

(65) Prior Publication Data

US 2005/0261194 A1    Nov. 24, 2005

(30) Foreign Application Priority Data

Oct. 9, 2001    (FR) .................................. 01 12984

(51) Int. Cl.
*A61K 38/08*    (2006.01)
*C07K 7/06*    (2006.01)

(52) U.S. Cl. ........................................ 514/15; 530/328
(58) Field of Classification Search .............. None
See application file for complete search history.

(56) References Cited

U.S. PATENT DOCUMENTS 4,301,065 A * 11/1981 Bach et al. ................. 530/328
5,112,810 A    5/1992 Nagai et al.
5,288,706 A    2/1994 Yamanouchi et al.
5,639,726 A * 6/1997 Lawrence et al. ............ 514/12
5,808,009 A * 9/1998 Robinson et al. ........... 530/413

FOREIGN PATENT DOCUMENTS

| IE | 51744 | 5/1981 |
|---|---|---|
| JP | 6192120 | 7/1994 |
| JP | 8003057 | 1/1996 |

OTHER PUBLICATIONS

Safieh-Garabedian et al., Neuroimmunomodulation 1999, vol. 6 pp. 39-44.*
Evers et al., J. Neurol. 1999, vol. 246, pp. 802-809.*
Dardenne et al., Contribution of zinc and other metals to the biological activity of the serum thymic factor, 1982, Proc. Natl. Acad. Sci. 79, 5370-5373.*
Pleau et al., Antagonistic analogue of serum thymic factor interacting with the FTS cellular receptor, 1979, Immunology Letters 1, 179-182.*
Bared Safieh-Garabedian, et al., "Potent analgesic and anti-inflammatory actions of a novel thymulin-related peptide in the rat," British Journal of Pharmacology, vol. 136, pp. 947-955, 2002.
Bared Safieh-Garabedian, et al., "Cytokine-Mediated or Direct Effects of Thymulin on the Nervous System as Assessed by Pain-Related Behavior," Neuroimmunomodulation, vol. 6, pp. 39-44, 1999.

* cited by examiner

*Primary Examiner*—Anish Gupta
*Assistant Examiner*—Ronald T Niebauer
(74) *Attorney, Agent, or Firm*—Buchanan Ingersoll & Rooney PC

(57) ABSTRACT

The present invention relates to the utilization of peptide analogues of thymulin that are inactive relative to the immune system, not comprising zinc and having anti-pain activity, for manufacturing a medicine for the treatment of pain.

4 Claims, 11 Drawing Sheets

USE OF THYMULIN-LIKE PEPTIDES FOR MAKING PAIN-RELIEVING MEDICINES

FIELD OF THE INVENTION

The invention relates to the utilization of peptide analogues of thymulin for use in manufacturing anti-pain medicines.

BACKGROUND OF THE INVENTION

The majority of acute or chronic pain results from an inflammatory reaction. The recommended treatments for reducing pain frequently consist of initially reducing the inflammatory reaction.

At the present time there are two main classes of anti-inflammatory medicines:
the non-steroidal anti-inflammatory agents (NSAIDs); and
the corticosteroids.

The NSAIDs and the corticosteroids have the drawback of combining an unpleasant side effect with their beneficial therapeutic effect (reduction of inflammation and pain).

In fact, the NSAIDs provoke the formation of ulcers while the corticosteroids have an immunosuppressive action.

The ideal analgesic anti-inflammatory medicine would be a medicine not having side effects nor an effect on physiology nor on the immune system.

In addition, there is a second type of pain that is not caused by inflammation. This neurogenic pain is, furthermore, characterized by its being refractory to traditional treatment, including opiates. Different treatment have been implemented such as the use of anti-inflammatories, anti-epileptics, anti-depressants, sympatholytic drugs or combinations of these.

However, neurogenic pain is very protean and consequently is very difficult to treat.

Because of these considerations, the medicines available today for treating pain are limited in number and are sometimes ineffective. This ineffectiveness can also be the result of an acquired tolerance to the product. So, the practitioner is obliged to modify his prescription. In order for this to be efficacious, there has to be another class of medicines available to him.

This explains the importance of the research in this field.

DESCRIPTION OF THE INVENTION

The peptide analogs of thymulin according to the present invention have already been described in the patents and certificate of addition FR 7715963, FR 7811870 and EP 0041019 as relates to medicines for the treatment of auto-immune diseases, stimulation of T cells and the prevention of graft rejection. The properties of these peptides relative to the immune system have been shown to be zinc-dependent. In fact, zinc contained in the peptide confers upon it a tetrahedral conformation, which corresponds to the active form of the molecule. In the absence of zinc, the peptide analogs would no longer have any activity. In addition, it has consequently been shown that these properties, demonstrated by in vitro assays, have no affect on the immune system at in vivo trials. Moreover, no secondary effects have been produced. These peptides are perfectly safe.

Numerous publications have shown that thymulin can, depending on the dose injected, induce or reduce hyperalgesia (Safieh-Garabedian et al., *Neuroimmunomodulation*, 6:39-44, 1999). At low doses (on the order of nanograms in the rat; that is 0.2 to 20 µg/kg), thymulin induces hyperalgesia, while at higher doses (on the order of micrograms in the rat; in other words 50-100 µg/kg), it reduces hyperalgesia. Utilization of thymulin was thus impossible, given its effect on the immune system and this dose-dependent (or biphasic) effect, inducing or reducing pain.

Accordingly, the inventors were interested in peptide analogues of thymulin that are inactive relative to the immune system. Although they did not exhibit the initially expected activity, they verified their spectrum of activity and confirmed that, against all expectations, they did not exhibit this ambivalent dose-dependent effect, that they had solely an analgesic activity, without being zinc dependent, and that finally, they were shown to be active in vivo.

The inventors' findings thus led them to provide, using these peptides whose safety had already otherwise been established, a new class of anti-pain medicines making it possible to treat pain of inflammatory and/or neurogenic origin.

The present invention relates to the utilization of peptide analogues of thymulin (TAP), which are inactive relative to the immune system and have analgesic activity, for manufacturing a medicine for the treatment of pain.

"Peptide analogues of thymulin inactive relative to the immune system" for the purpose of this application are defined as peptide analogues of thymulin that are inactive relative to the T-cell specific immune response. In particular, these peptides do not form complexes with metals such as zinc, for example. (Dardenne et al., *PNAS*, 79: 5370-5373, 1982)

Utilization of the peptides according to the invention has the advantage of being effective against pain without inducing adverse secondary effects.

These peptides are otherwise efficacious at doses from 10 to 100 times lower than those of classical analgesics. For example, in the rat, the doses utilized are on the order of 1 µg per rat (or 5 µg/kg) versus 4 mg/kg for non-steroidal anti-inflammatory drugs and 200 mg/kg for steroidal anti-inflammatory drugs. Activity was also found at lower doses on the order of 50 to 200 ng/rat; that is from 0.25 to 1 µg/kg.

In particular, the peptides utilized according to the invention have the following sequence:

X-Gln-Gly-Gly-Ser-Asn (SEQ ID NO: 47)
wherein X represents Ser, Lys-Ser, Ala-Lys-Ser, Glu-Ala-Lys-Ser (SEQ ID NO: 48), Gln-Ala-Lys-Ser (SEQ ID NO: 49), PyroGlu-Ala-Lys-Ser (SEQ ID NO: 50), as well as any derived sequence comprising 1 or 2 modified amino acids, said possible modifications being of the following type:

PyroGlu: D-PyroGlu, Glu, Gln

Gln: Z-Gln, D-Gln, Pro, Cys (S—CONH2), Met(O), Glu, Glu(γ-cyano), Glu(γCS—NH2), D-Glu, Asn, NorVal Ala: D-Ala, Z-Ala, Ac-Ala Lys: Arg, D-Lys, N-γ-Z-Lys, Lys(N6 acetyl), Orn, Har, 2-amino-hexanoyl, 2,6-diamino-hexynoyl, 2,6-diamino-hexenoyl, Hep, D-Lys(N6-acetyl)

Ser: Ala, (N-methyl)Ser, D-Ser, Thr

Gly: Ala, Ser, D-Ala, D-Leu

Asn: CyanoAla, Thio-Asn, Asp, Gln, Glu, β-Ala-NH2, D-Asn, Asn-NH2

Reference to the "thymulin analogues" clearly excludes thymuline, the peptide having the following sequence: Pyro-Glu-Ala-Lys-Ser-Gln-Gly-Gly-Ser-Asn (SEQ ID NO: 46).

In particular, the invention envisages protection of utilization of the following peptides:

(1) PyroGlu-Ala-Lys-Ser-Gln-Gly-Gly-Ser-Asp (SEQ ID NO: 1)
(2) PyroGlu-Ala-Lys-Ala-Gln-Gly-Gly-Ser-Asn (SEQ ID NO: 2)
(3) PyroGlu-Ala-Lys-Ser-Gln-Gly-Gly-Ser-Gln (SEQ ID NO: 3)
(4) PyroGlu-Ala-Lys-Ser-Gln-Gly-Gly-Ser-β-Ala-NH2 (SEQ ID NO: 4)
(5) PyroGlu-Ala-Lys-Ser-Gln-Gly-Gly-Ser-D-Asn (SEQ ID NO: 5)
(6) PyroGlu-Ala-Lys-Ser-Gln-Gly-Gly-Ser-Asn-NH2 (SEQ ID NO: 6)
(7) PyroGlu-Ala-Lys-Ser-Asn-Gly-Gly-Ser-Asn (SEQ ID NO: 7)
(8) PyroGlu-Ala-Lys-Ser-Nva-Gly-Gly-Ser-Asn (SEQ ID NO: 8)
(9) PyroGlu-Ala-Lys-Ser-Gln-Gly-Gly-Ala-Asp (SEQ ID NO: 9)
(10) Gln-Ala-Lys-Ser-Gln-Gly-Gly-Ser-Asp (SEQ ID NO: 10)
(11) Gln-Ala-Lys-Ala-Gln-Gly-Gly-Ser-Asn (SEQ ID NO: 11)
(12) Gln-Ala-Lys-Ser-Gln-Gly-Gly-Ser-Gln (SEQ ID NO: 12)
(13) Gln-Ala-Lys-Ser-Gln-Gly-Gly-Ser-β-Ala-NH2 (SEQ ID NO: 13)
(14) Gln-Ala-Lys-Ser-Gln-Gly-Gly-Ser-D-Asn (SEQ ID NO: 14)
(15) Gln-Ala-Lys-Ser-Gln-Gly-Gly-Ser-Asn-NH2 (SEQ ID NO: 15)
(16) Gln-Ala-Lys-Ser-Asn-Gly-Gly-Ser-Asn (SEQ ID NO: 16)
(17) Gln-Ala-Lys-Ser-Nva-Gly-Gly-Ser-Asn (SEQ ID NO: 17)
(18) Gln-Ala-Lys-Ser-Gln-Gly-Gly-Ala-Asp (SEQ ID NO: 18)
(19) Glu-Ala-Lys-Ser-Gln-Gly-Gly-Ser-Asp (SEQ ID NO: 19)
(20) Glu-Ala-Lys-Ala-Gln-Gly-Gly-Ser-Asn (SEQ ID NO: 20)
(21) Glu-Ala-Lys-Ser-Gln-Gly-Gly-Ser-Gln (SEQ ID NO: 21)
(22) Glu-Ala-Lys-Ser-Gln-Gly-Gly-Ser-β-Ala-NH2 (SEQ ID NO: 22)
(23) Glu-Ala-Lys-Ser-Gln-Gly-Gly-Ser-D-Asn (SEQ ID NO: 23)
(24) Glu-Ala-Lys-Ser-Gln-Gly-Gly-Ser-Asn-NH2 (SEQ ID NO: 24)
(25) Glu-Ala-Lys-Ser-Asn-Gly-Gly-Ser-Asn (SEQ ID NO: 25)
(26) Glu-Ala-Lys-Ser-Nva-Gly-Gly-Ser-Asn (SEQ ID NO: 26)
(27) Glu-Ala-Lys-Ser-Gln-Gly-Gly-Ala-Asp (SEQ ID NO: 27)
(28) Ala-Lys-Ser-Gln-Gly-Gly-Ser-Asp (SEQ ID NO: 28)
(29) Ala-Lys-Ala-Gln-Gly-Gly-Ser-Asn (SEQ ID NO: 29)
(30) Ala-Lys-Ser-Gln-Gly-Gly-Ser-Gln (SEQ ID NO: 30)
(31) Ala-Lys-Ser-Gln-Gly-Gly-Ser-β-Ala-NH2 (SEQ ID NO: 31)
(32) Ala-Lys-Ser-Gln-Gly-Gly-Ser-D-Asn (SEQ ID NO: 32)
(33) Ala-Lys-Ser-Gln-Gly-Gly-Ser-Asn-NH2 (SEQ ID NO: 33)
(34) Ala-Lys-Ser-Asn-Gly-Gly-Ser-Asn (SEQ ID NO: 34)
(35) Ala-Lys-Ser-Nva-Gly-Gly-Ser-Asn (SEQ ID NO: 35)
(36) Ala-Lys-Ser-Gln-Gly-Gly-Ala-Asp (SEQ ID NO: 36)
(37) Lys-Ser-Gln-Gly-Gly-Ser-Asp (SEQ ID NO: 37)
(38) Lys-Ala-Gln-Gly-Gly-Ser-Asn (SEQ ID NO: 38)
(39) Lys-Ser-Gln-Gly-Gly-Ser-Gln (SEQ ID NO: 39)
(40) Lys-Ser-Gln-Gly-Gly-Ser-β-Ala-NH2 (SEQ ID NO: 40)
(41) Lys-Ser-Gln-Gly-Gly-Ser-D-Asn (SEQ ID NO: 41)
(42) Lys-Ser-Gln-Gly-Gly-Ser-Asn-NH2 (SEQ ID NO: 42)
(43) Lys-Ser-Asn-Gly-Gly-Ser-Asn (SEQ ID NO: 43)
(44) Lys-Ser-Nva-Gly-Gly-Ser-Asn (SEQ ID NO: 44)
(45) Lys-Ser-Gln-Gly-Gly-Ala-Asp (SEQ ID NO: 45)

More specifically, the invention envisages protection of utilization of the following peptides:

(19) Glu-Ala-Lys-Ser-Gln-Gly-Gly-Ser-Asp (SEQ ID NO: 19)
(1) PyroGlu-Ala-Lys-Ser-Gln-Gly-Gly-Ser-Asp (SEQ ID NO: 1)
(10) Gln-Ala-Lys-Ser-Gln-Gly-Gly-Ser-Asp (SEQ ID NO: 10)
(28) Ala-Lys-Ser-Gln-Gly-Gly-Ser-Asp (SEQ ID NO: 28)
(37) Lys-Ser-Gln-Gly-Gly-Ser-Asp (SEQ ID NO: 37)

These peptides have been studied in two models of inflammation and hyperalgesia in the rat, which were induced either by intraplantar injections (localized) or by intraperitoneal injections (systemic) of endotoxins. Pretreatment using these peptides dose—dependently abolishes both mechanical hyperalgesia and thermal hyperalgesia. In addition, pretreatment significantly reduces hyperproduction of IL-1β, IL-6, TNFα and NGF due to an intraplantar injection of endotoxin. In the case of intraperitoneal injection, which has the effect of a state comparable to septic shock (pain, fever, somnolence and anorexia), pretreatment prevents hyperalgesia and maintains the body at normal temperature.

Finally, these peptides have analgesic effects that are identical or superior to those of the other anti-inflammatory drugs, while not inducing any obvious change in physiological or behavioral parameters for all of the doses used.

Thus, these peptides have analgesic and/or anti-inflammatory properties.

The analgesic properties of these peptides extend also to neurogenic pain (or neuropathic pain). Several models have been used to test neurogenic pain of different etiologies: two animal models of mono-neuropathy, another pain model of the somatic or visceral type. These models have made it possible to confirm a significant reduction of the mechanical allodynia and, at times, thermal allodynia. The neuropathic manifestations are inhibited, while behavior associated with pain induced by the injection of irritating substances (capsaicin) is reduced. In all cases, these peptides have inhibitory effects that are greater or equal to those induced by other treatments utilized in cases of neurogenic pain.

Considering their properties, the utilization of these peptides is more particularly recommended in the treatment of migraine, sciatica, neuropathy and acute or chronic pain of inflammatory origin.

For optimum efficacy, the doses administered must be between 0.01 and 1 mg/kg, said administration being done by any variety of routes, including the parenteral, transcutaneous or nasal.

Other features and advantages of the invention will be better understood in view of the following examples, while referring to the figures representing, respectively:

EXAMPLES

Example 1

Figure 1:
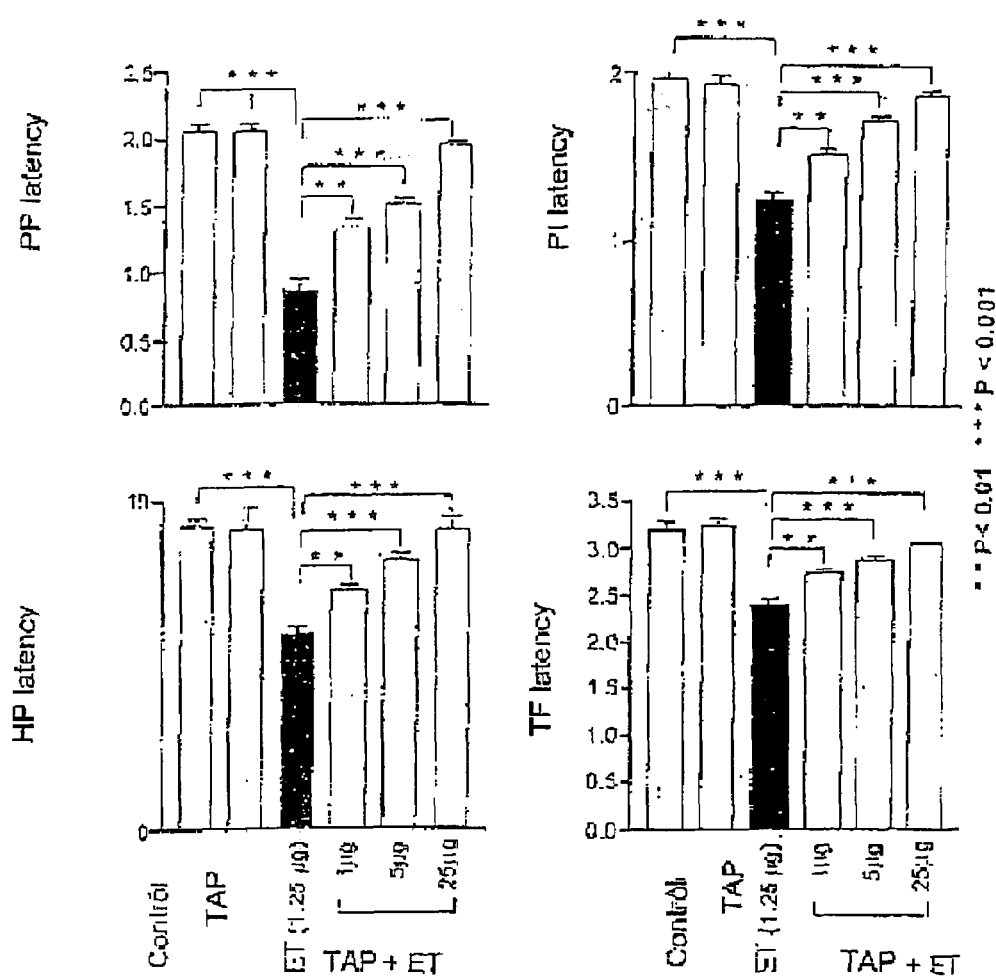
FIG. 1 represents the dose-dependent reduction of hyperalgesia induced by an injection of endotoxins.

Analgesic and Anti-Inflammatory Properties of the Peptides According to the Invention 1. Material and Methods:

The experiments were conducted using adult, male Sprague-Dawley rats weighing between 200 and 250 g. The animals were reared under optimum conditions of light and temperature (12 h light and shadow cycle; 22±3° C.). Food and water were dispensed ad libitum. All of the experiments were conducted in compliance with the ethical directives relative to pain experiments done on animals in the conscious state (Zimmermann M., 1983, *Ethical guidelines for investigations of experimental pain in conscious animals*, Pain, 16:109-110) and they were approved by the Institutional Review Board for animal care.

Behavioral Procedures

Thermal and mechanical pain tests were done over a period of 3 consecutive days prior to the injections, in order to establish a baseline.

The mechanical nociceptive threshold was determined by the mechanical paw pressure test (PP), while that of the thermal nociceptive threshold was determined using the hot-plate (HP), the paw immersion in hot water (PI) and the tail flick (TF) tests.

The PP test is done by applying a constant pressure of 0.20 g/cm$^2$ alternatingly to the left and right hind paws in an interval of 5 minutes between 2 consecutive pressure applications. The pressure is stopped when that animal exhibits a typical reaction characterized by a vigorous flexion reflex.

In the HP test, the animals are placed individually on a hot plate (52.5° C.±0.3° C.). The pain threshold is measured by the latency period lapsed between the moment, at which the animal is placed on the hot plate and the first sign of pain, indicated by the fact that the animal licks the paw or jumps.

In the PI test, the hind paws are wetted alternately in distilled water at 48° C. and the latency time lapsed until the first sign of withdrawal of the paw is noted.

In the TF test, the tail of each animal is immersed in distilled water at 50.5° C. The latency time taken by the animal to withdraw it is noted. The results are based on 3 consecutive trials done in 5 minute intervals.

Administration of the Drugs

Inflammatory hyperalgesia was done using two animal models: one for localized inflammation; the other for systemic inflammation.

In the so-called localized model, the rats received an intraplantar injection of a solution (1.25 µg in 50 µl of 9‰ physiological saline solution) of endotoxin (*Salmonella typhasa* lipopolysaccharides, Sigma) into one of the hind paws, which induces both thermal and mechanical hyperalgesia restricted to the paw having received the injection.

In the second model, the rats received an intraperitoneal injection of endotoxin (25 µg in 100 µl of physiological saline solution).

Various treatments are then possible:

Protocol 1(a): different groups of rats (n=5 in each group) were treated with the analogue peptide (TAP) Glu-Ala-Lys-Ser-Gln-Gly-Gly-Ser-Asp (SEQ ID NO: 19) (synthesized by Quantum Biotechnologies, Inc., Canada), in the following fashion:

either, they received one intraperitoneal injection (25 µg in 50 µl of physiological saline solution) of this peptide;

or, they were pretreated with different doses of this peptide (1.5 and 25 µg in 50 µl of sodium chloride) by intraperitoneal injection, 30 minutes prior to injection of endotoxins (ET) (1.25 µg in 50 µl of physiological saline solution by intraplantar injection).

Protocol 1(b): other experiments looked at comparing the efficacy of the analog peptides with that of steroids, NSAIDs and peptides known for their antagonism of the hyperalgesia induced by IL-1β and the prostaglandins.

One group of rats was pretreated with intraperitoneal injections of Lys-D-Pro-Thr (10 mg/kg) in 100 µl of physiological saline solution, 30 minutes prior to injection of TAP. This tripeptide is known for its antagonism of the hyperalgesia induced by IL-1β only.

In the second group, the rats received intraperitoneal injections of the Lys-D-Pro-Val tripeptide (10 mg/kg) in 100 µl of saline solution, 30 minutes prior to the injection of TAP. Lys-D-Pro-Val is an antagonist of the hyperalgesia induced by IL-1β and $PEG_2$.

The doses utilized for these tripeptides are those described in the article by Safieh-Garabedian (Safieh-Garabedian B., Kanaan S. A., Haddad J. J., Abou Jaoude P., Jabbur S. J., Saade N. E. 1997, *Involvement of interleukin-1β, nerve growth factor and prostaglandin-E2 in endotoxin induced localized inflammatory hyperalgesia*. Brit. J. Pharmacol. 121: 1619-1626).

A third and a fourth group were treated with dexamethasone and indomethacin.

Dexamethasone phosphate dissolved in a 9‰ sodium solution was injected, at a concentration of 200 µg/kg, just before and 3 hours after the injection of ET.

Indomethacin was prepared by dissolving the indomethacin lactose in a saline buffer solution (pH 7.4) and was injected at a concentration of 4 mg/kg, just before and 3 hours after the injection of ET.

All of the tests of the aforementioned experiments were done 9 hours after injection of the ET. This coincides with the hyperalgesia peak in this model. The injection of saline solution (50-100 µl intraplantar) did not demonstrate significant alteration of the pain threshold.

Protocol 2(a): One group of rats received one intraperitoneal injection of ET (50 µg), while the other group was pretreated with the protein analogue of thymulin (TAP) (25 µg, intraperitoneal injection), 30 minutes before the injection of ET.

The TF and PP tests were then done at 1 hour, 3 hours and 6 hours after the injection of ET.

Protocol 2(b): Different groups of rats (n=5 in each group) were treated in the following fashion:

either they received one intraperitoneal injection of 50 µg of ET, or they were pretreated with the TAP peptide (25 µg, intraperitoneal injection), 30 minutes before an injection of endotoxin.

Rectal temperature was measured at 1 hour, 3 hours and 6 hours.

A control group received an intraperitoneal injection of TAP peptide (25 µg dissolved in 100 µl of saline solution).

Cytokines and Nerve Growth Factor (NGF)

These experiments required tissue sampling. The animals were sacrificed by anesthesia (sodium penthiobarbital, 50 mg/kg) and the skin of the hind paws is sampled either at 1 h (for the determination of the TNFα) or at 4 h (for the determination of IL-1β, IL-6 and NGF) after the endotoxin injection.

These tissue samples are weighed and then quick frozen and stored at −70° C. with a view of proceeding with the evaluation of IL-1β, TNFα, IL-6 and NGF.

In another series of experiments, the tissues are taken as described above using different groups of rats; the one group being pretreated with TAP 30 minutes before injection of ET and the other group having been injected with TAP only.

The tissues are homogenized in a phosphate buffer solution (PBS, pH=7.4), containing 0.4 M of NaCl, 0.05% of Tween-20®, 0.5% bovine serum albumin (BSA), 0.1 mM of phenylmethylsulfonyl fluoride, 0.1 mM of benzethonium chloride, 10 mM of EDTA and 20 KI/mL of aprotinin.

The mixture is then centrifuged at 1,200 g for 60 minutes at 4° C. The cytokines and the NFG contained in the supernatant were measured using ELIZA assays.

The NGF is measured with the aid of an immunological kit (Promega) by following the recommended instructions of the manufacturer.

Measurement of the IL-1β, TNF-α and IL-6 was done in accordance with the protocols described by Safieh-Garabedian (Safieh-Garabedian B., Dardenne M., Kanaan S. A., Atweh S. F., Jabbur S. J., Saadé N. E. 2000. *The role of cytokines and prostaglandin-E2 in thymulin induced hyperalgesia*. Neuropharmacology 39:1653-1661).

Statistical Analysis and Treatment of the Data

A pain threshold value for the different nociceptive tests was defined for each group of animals. The data obtained for each drug tested were compared either to the control established before the injection or with two types of controls: a series of animals receiving one injection of ET and another series of animals receiving one injection of 9‰ sodium chloride solution.

For the evaluation of the cytokine and NFG levels, the values obtained using the animals injected with ET alone, drug alone or ET plus drug were compared to the values obtained using the groups of control animals injected with a 9‰ sodium chloride solution.

The significance of the standard deviation was established using ANOVA followed by a Bonferroni test.

2. Results

Effect of the TAP Peptide on Inflammatory Hyperalgesia Induced by Intraplantar Injection of ET.

The intraplantar injection of ET (1.25 µg in 50 µl of saline solution) into the hind paw of rats induced a significant reduction of the nociceptive thresholds measured at 9 h (peak of hyperalgesia) according to the PP test (0.87±0.09 s compared with 2.06±0.06 s for the control saline solution, P<0.001) for mechanical hyperalgesia and according to the PI test (1.25±0.04 s compared with 1.97±0.05 s for the control saline solution, P<0.001), HP (6.0±0.18 compared with 9.24±0.16 s for the control saline solution, P<0.001) and TF (2.40±0.06 s compared with 3.19±0.08 s for the control saline solution, P<0.001) for thermal hyperalgesia. Treatment using the TAP peptide (1.5 and 25 µg) reduced in dose—dependent fashion the hyperalgesia induced by the injection of ET (FIG. 1). With the 25 µg dose of TAP, the latency for triggering the various responses were from 2.05±0.07 s, 1.94±0.005 s, 9.12±0.7 s and 3.22±0.09 s for the PP, PI, HP and TF tests, respectively (p>0.05 for all of the values in comparison with the baseline or with the values obtained using saline solution). Intraperitoneal injection of TAP alone (25 µg in 50 µl of saline solution) did not result in significant change in the latency time in the different pain tests.

Figure 2:
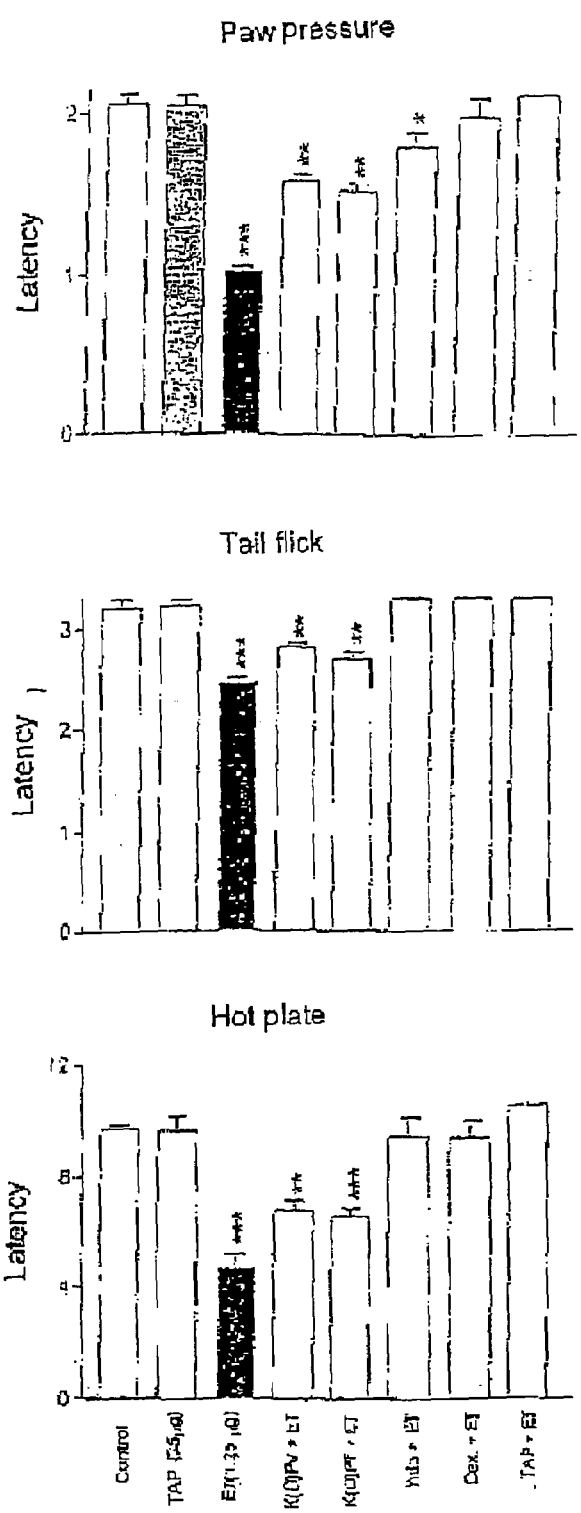
FIG. 2 represents a comparative study of the anti-hyperalgesic effects of the peptides according to the invention compared with steroids, non-steroidal anti-inflammatories and analgesic tri-peptides.

Comparison of the Efficacy of the Tap Peptide with Other Medicines and Analogues When the effect of TAP on hyperalgesia induced by an intraplantar injection of ET (1.25 µg) is compared with the effects obtained using a steroid, an NSAID and the Lys-D-Pro-Val et Lys-D-Pro-Thr peptides, the results obtained demonstrate that TAP is a much more efficacious analgesic agent than the Lys-D-Pro-Val et Lys-D-Pro-Thr peptides (FIG. 2). TAP has effects similar to those of indomethacin and dexamethasone but at much lower concentrations (FIG. 2).

Effect of TAP on the Cytokines

Injection of endotoxins into the hind paw of rats induced a significant increase (p<0.001) of the pro-inflammatory cytokine and NGF concentrations and in comparison with the rats injected with saline solution or with the paws of the same rats not having received any product. One hour after injection of ET, the concentration of TNF-α was 345.0±61.0 pg/paw compared with 100.0±8.00 pg/paw after injection of control saline solution. Three hours after injection of ET, the concentration of IL-1β was 2,850.6±255.4 pg/paw compared with 400.0±45.0 pg/paw after injection of the control saline solution; the concentration of IL-6 was 2,831.0±285.0 pg/paw compared with 250.0±50.0 pg/paw for the control saline solution and the NGF concentration was 23.0±1.73 ng/paw compared with 9.11±1.6 ng/paw for the control saline solution.

Figure 3:
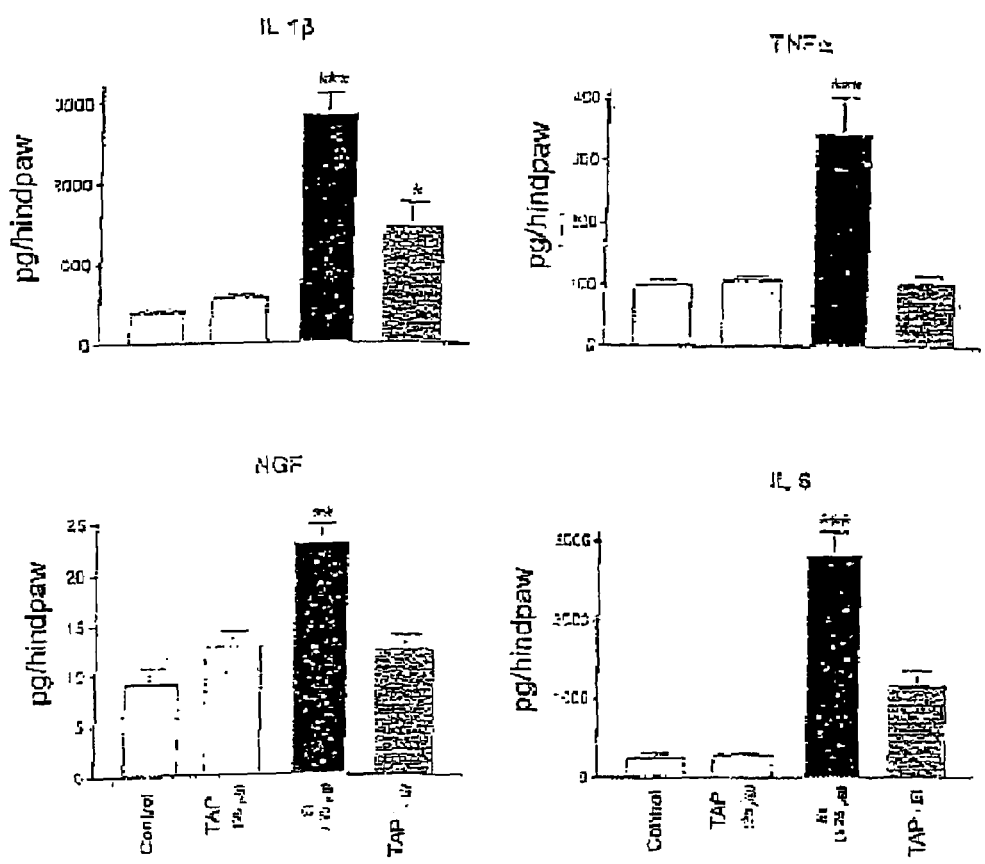
FIG. 3 represents the anti-inflammatory effects of pretreatment with the peptides according to the invention, by reduction of the concentrations of pro-inflammatory cytokines and NGF.

Previous treatment with TAP nullified the increase of the TNF-α concentration and significantly reduced the IL-1β concentrations (from 2850.6±255.4 to 1686.0±266.0 pg/paw, P<0.01), IL-6 (from 2831±285 to 1158±197.0 pg/paw, p<0.001) and NGF (from 23.0±1.73 to 16.73±2.70 ng/paw, p<0.001) (FIGS. 3A, B, C and D). Injection of TAP (25 µg) in control animals did not induce significant change of the cytokine or NGF concentrations, as shown in FIG. 3.

Effect of TAP on Systemic Inflammatory Hyperalgesia Induced by ET.

Figure 4:
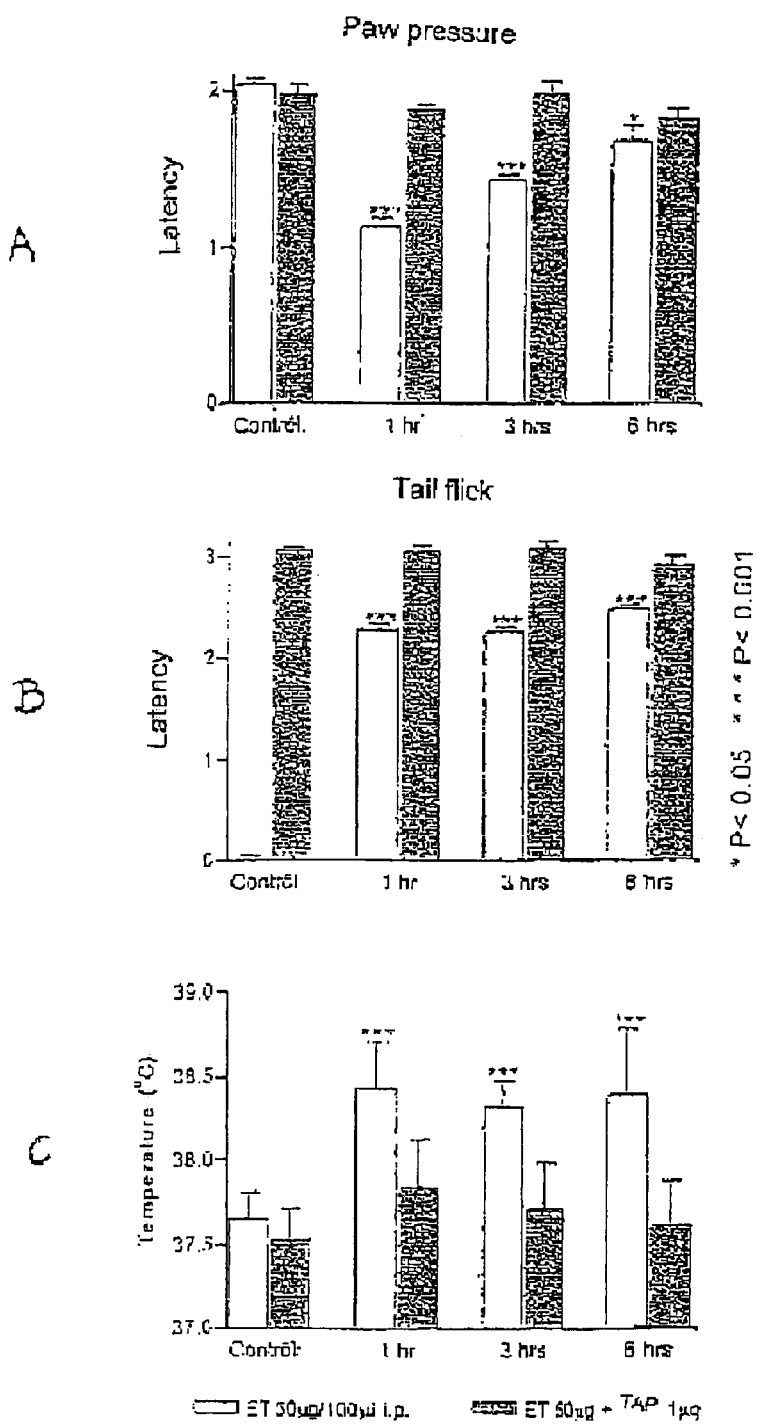
FIG. 4 represents the effects of pretreatment relative to pain (A and B) and to fever (c) induced by systemic injection of endotoxins in simulation of septic shock.

Injections of ET (50 µg, i.p.) caused a significant reduction of the nociceptive thresholds at one hour according to the PP test (1.13±0.06 compared with 2.03±0.04 s for the controls, p<0.001) and according to the TF test (2.27±0.06 compared with 3.08±0.04 s for the controls, p<0.001). Hyperalgesia remained observable for six to nine hours after the injection (FIGS. 4A and 4B). Previous treatment by intraperitoneal injection of TAP (25 µg) thirty minutes before systemic administration of ET abolished the mechanical hyperalgesia (FIG. 4A) and the thermal hyperalgesia (FIG. 4B) produced by the ET.

Endotoxin is a known pyrogen and its injection induced an significant increase in body temperature at one hour (38.43±0.028° C. compared with 37.65±0.16° C. for the controls). The temperature then remained significantly elevated at six hours (FIG. 4C). Previous treatment with TAP in intraperitoneal injection (25 µg) nullified the process of increase of body temperature induced by ET and the values were not significantly different from those of the controls (FIG. 4C).

Example 2

Analgesic Properties of a Peptide According to the Invention (TAP) Relative to Pain of Neurogenic Etiology 1. Material and Methods:

Adult male Sprague-Dawley rats (250-300 g) were used for these trials. Over the period of the experiments, the rats were placed under standard conditions (4 to 5 individuals to a cage, 12 hour day/night cycle, 22.2° C.), with free access to water and food. The necessary surgical procedures were done under deep anesthesia using ketamine (KETALAR®, 40-50 mg/kg, intraperitoneal injection), preceded by pre-anesthesia using chlorpromazine (8 mg/kg, idem) and atropine (0.05 mg/kg, idem).

This study was based on two experimental protocols for the induction of pain of neurogenic etiology. The first protocol utilized two animal models of mononeuropathy. The second protocol was based on the injection of capsaicin, a substance known to activate the specific afferent fiber groups implicated in nociceptive signaling.

a) Protocol I: Animal Models of Mononeuropathy

Induction of Mononeuropathy:

Mononeuropathy was induced in different groups of rats (n=6 rats in each group) according to the CCI (chronic constriction injury, chronic nerve constriction, Bennet G. J. et Xie Y. K., 1988, *A peripheral mononeuropathy in rat that produces disorders of pain sensation like those seen in man*, Pain, 33:87-107) or according to the SNI (spared nerve injury, spared nerve of the enervated paw, Decosterd I. et Woolf C. J., 2000, *Spared nerve injury: an animal model of persistent peripheral neuropathic pain*, Pain, 87:149-158). The sciatic nerve was exposed after dissection of the posterior hip and by incision through the skin and the fatty layer covering the popliteal fossa. For the CCI model, four loose ligatures (chromed catgut 4.0) were placed on the proximal side of the sciatic trifurcation. For the SNI model, the external popliteal sciatic nerve and the internal popliteal sciatic nerve were isolated, tightly ligatured and sectioned, while the sural nerve innervating the lateral aspect of the paw was left intact.

Behavioral Tests:

The rats were placed in individual compartments of one cage, whose floor was made of a metal grating allowing access to the heel pad and to the lateral aspect of the paw with wires.

For mechanical allodynia, the plantar surface of the hind paws (lateral surface for the SNI model and the median plantar surface for the CCI) was contacted with the von Frey wires (VFF 4.31 and 5.07, Stoelting Co., USA), which corresponded to the forces of 2.041 and 11.749 g (18.5 and 106.7 mN), respectively. The flexion forces of these wires were shown to be insufficient for causing nociceptive withdrawal reflexes in normal animals. The number of paw retractions induced by 10 trials was established for each rat on each hind paw prior to (baseline) and after induction of the mono-neuropathy. In normal rats, the low caliber wires (VFF 4.31) and higher caliber (VFF 5.07) induced an average 1.3±0.2 and 2.7±0.3 responses/10 trials, respectively.

After induction of neuropathy, the two filaments produced more than 5 responses/10 trials.

The method described by Choi et al. (1994, *Behavioral signs of ongoing pain and cold allodynia in a rat model of neuropathic pain*, Pain, 59:369-376) was used for evaluation of cold allodynia. It consists of applying several drops (approximately 50 µl) of an acetone solution on the paw and measuring the duration of the retraction reaction. One half second and 20 seconds are the values chosen arbitrarily for the minimum and maximum threshold, respectively.

The duration (D) of retraction of the paw (RP) in response to a nociceptive ray of radiant heat oriented towards the plantar surface was established in the normal rat. Increasing the DRP after induction of the mononeuropathy was considered to be an indication of hyperalgesia. Each rat underwent two RP tests per session a minimum of every five minutes.

The neuropathic manifestations were at maximum seven to ten days after induction of the neuropathy. The effects of the injections of TAP were tested during this period, which corresponds to the peak of the neuropathy.

b) Protocol II: Chemical Irritation of the Nociceptive Afferents

This protocol was based on the established properties of capsaicin, which selectively irritates a specific group of afferent fibers (called "capsaicin sensitive primary afferents" or CSPA) known to produce a neurogenic inflammation and for transmitting the nociceptive information (for a review, see Szolcsany J., 1996, *Neurologic inflammation: reevaluation of axon reflex theory*, In: Geppetti P. and Holzer P. (Eds.), Neurogenic Inflammation, pp. 33-42. CRC Press, Boca Raton).

Our group applied two methods: intra-plantar (i. pl.) and intraperitoneal (i.p.) injection in low quantities of capsaicin in order to provoke reversible somatic and visceral pain, respectively.

Intraplantar Injection of Capsaicin

Injection of capsaicin (10 µg in 50 µl of a 10% solution of Tween 20 in olive oil) produced hyperalgesia, whose peak was at three to six hours after injection and which disappeared at the end of 24 hours. Mechanical hyperalgesia was evaluated using the paw pressure test (PP), which consists in applying a constant pressure of 0.2 kg/cm on the dorsal part of the hind paw. The time lapsed between the application of the pressure and the nociceptive reflex of retraction of the paw was considered as the latency time (or threshold) of mechanical nociceptive. Thermal hyperalgesia was evaluated using the hot-plate (HP) test and the paw immersion (PI) test.

The HP and PI tests were done as in Example 1, the hot-plate having a temperature 52.5±0.3° C. and the hot water container at 48±0.3° C.

The PP and PI tests were done one after the other on the two hind paws observing an interval of five minutes between two consecutive tests.

The rats were sent to the laboratory one week prior to injection so that they would become accustomed to the environment and the tests were done on the rats over two or three days in order to obtain the baseline value for each test before any treatment (detailed description in Kanaan S. A. et al., 1996, *Endotoxin-induced local inflammation and hyperalgesia in rats and mice: a new model for inflammatory pain*, Pain, 66:373-379).

Intraperitoneal Injection of Capsaicin

This test consisted of injecting (i.p.) 20 µg of capsaicin in 100 µl of a 10% solution Tween 20 in olive oil in some rats and observing the behavior induced by these injections. A 4-level behavioral scale was designed according to the method described by Giesler G J et al., (1976, *Inhibition of visceral pain by electrical stimulation of the periaqueductal gray matter*, Pain 2:43-48).

The levels were defined as follows: 0=normal behavior; 1=slight contraction of the abdominal muscles; 2=contraction of one single side and luxation of the haunch dropping; 3=significant contraction of the abdominal muscles and extension of the two rear paws.

For the evaluation of the animals' behavior, each rat was placed in transparent cage placed over a mirror inclined at 450 for optimum observation.

Normal and nociceptive behaviors were noted by one observer using a polygraph and the time corresponding to each level over a period of 30 minutes was accounted for regarding the polygraph recordings by another observer. None of the two observers knew the injection administered nor the expected effects.

Medicines Injected

The TAP peptide used is the same as that used in Example 1.

The capsaicin (8-methyl-N, vanillyl-nonanamide, Sigma #M1022) was dissolved in a 10% solution of Tween 20 in olive oil and administered i.p. or i.pl. at the appropriate concentration.

Analysis of the Data

During the experiments done on rats suffering from neuropathy, allodynia and hyperpathy were evaluated in each group of animals with reference to the baseline condition established prior to induction of mononeuropathy. For example, the average of the number of paw withdrawal induced by each VFF was calculated for all of the rats of each group and the variation of this mean has been determined after treatment with TAP at different time periods after the injection. The same method has been followed for allodynia in the code and the hypertrophy relative to heat.

In the course of the experiments involving the injection i.p. of capsaicin, the mean of the measurements done using each pain test (PP, HP or PI) was calculated for each group of rats prior to the injection of the capsaicin (baseline condition) and at different time intervals after injection (3, 6, 9 and 24 hours). TAP was injected (i.p.) thirty minutes before the capsaicin and the latency times of the different pain tests were measured at the same intervals of time after injection of the capsaicin.

For the injection i.p. of the capsaicin, the total time corresponding to each behavioral level was measured for the animals having received the capsaicin alone or the capsaicin after the TAP. The variation of the neuropathic manifestations or of the pain tests after the treatments were evaluated by ANOVA then by Bonfrerroni tests done post hoc. The variations of the pain scores with or without treatment were evaluated by the Student bilateral test by assuming a significance level of 5% ($p<0.05$).

2. Results

Effects of the Injection of Tap on Neuropathic Manifestations

Figure 5:
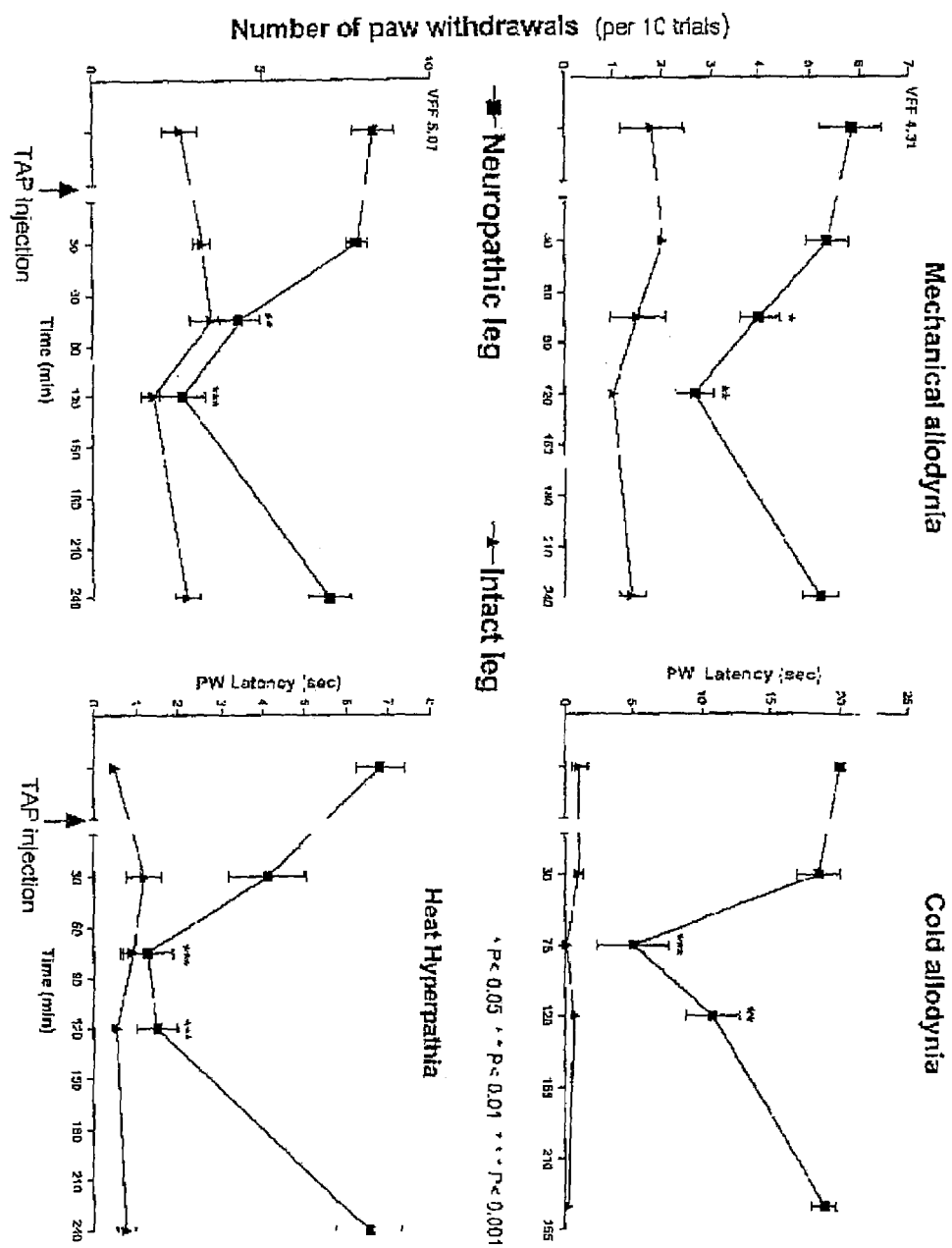
FIG. 5 represents the inhibition of allodynia (abnormal pain induced by inoffensive stimuli) and hyperpathy (exaggerated reaction to a nociceptive stimulation of moderate intensity) in rats with a CCI (chronic compression of the sciatic nerve) mono-neuropathy, pretreated with the peptides according to the invention.
Figure 6:
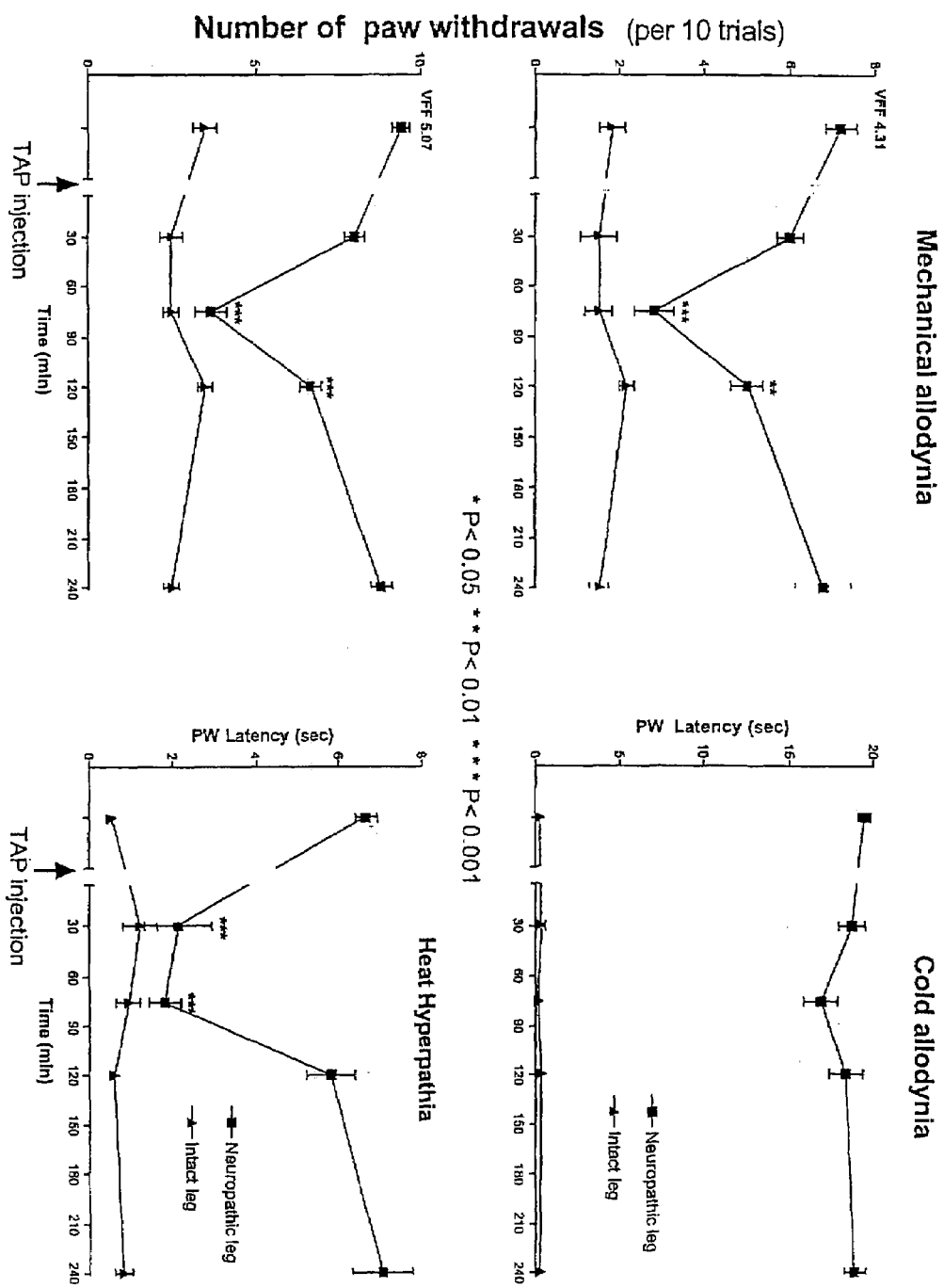
FIG. 6 represents the inhibition of allodynia and hyperpathy in rats with an SNI (spared nerve pain of a enervated paw) mononeuropathy, pretreated with the peptides according to the invention.

Injection of TAP (5 µg in 100 µl, i.p.) in rats of two groups (n=6 rats per group) subjected to neuropathy induced by CCI or SNI resulted in a significant attenuation of all of the neuropathic manifestations (FIGS. 5 and 6). This effect was maximum for mechanical allodynia at two hours after injection. It was maximum for cold allodynia at 75 minutes after injection and the hyperpathy in the CCI model and for all of the neuropathic manifestations in the SNI model. However, the cold allodynia was only moderately reduced by TAP in the SNI model. Reversibility of the effects of TAP was observed three to four hours after injection.

Figure 7:
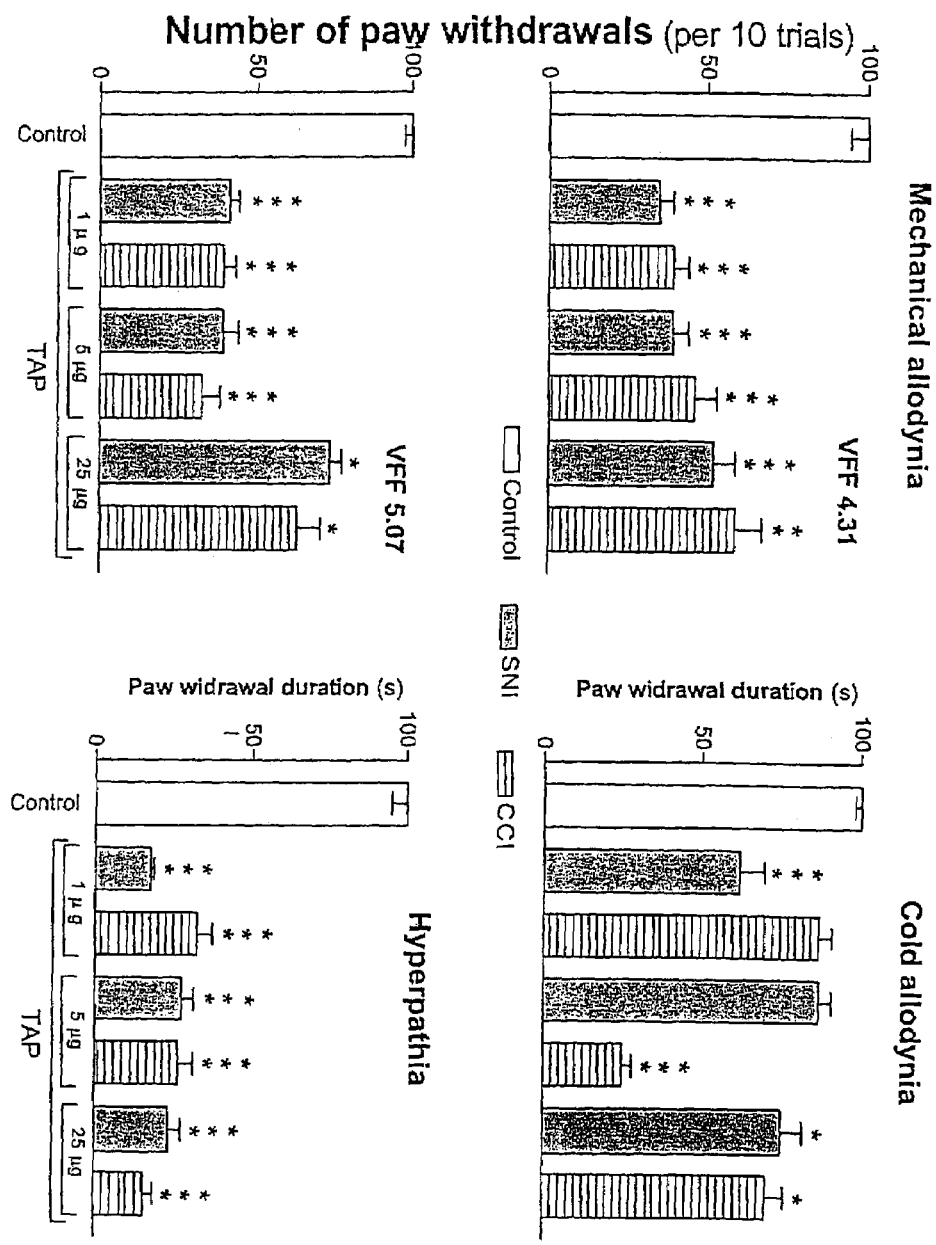
FIG. 7 represents a dose study of the peptides according to the invention in rats having the two aforementioned types of neuropathy.

The effects of doses of TAP of 1 and 25 µg were evaluated in other groups of rats by following the two models. FIG. 7 shows that the attenuation of the neuropathic manifestations was maximal using a dose of 5 µg/rat.

Figure 11:
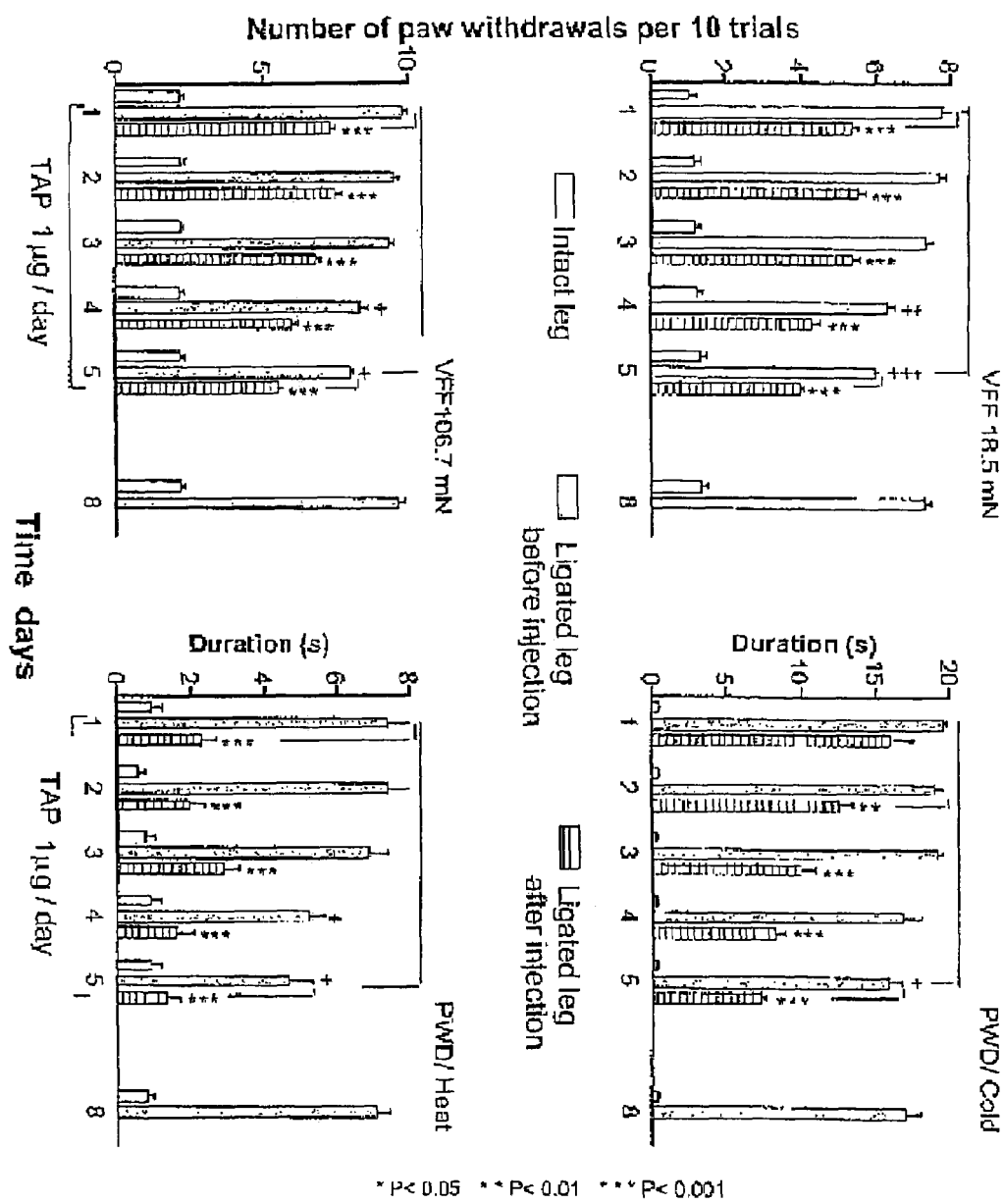
FIG. 11 represents the results of daily treatment using TAP.

Daily treatment with TAP (1 µg in 100 µL) over 5 consecutive days produces a progressive reduction of the manifestations of the allodynia as well as a potentiation of the effects of each injection. The most obvious proof of this potentiation is the increased inhibition of the cold allodynia that was little changed by a single injection of TAP (cf. FIG. 11).

Figure 10:
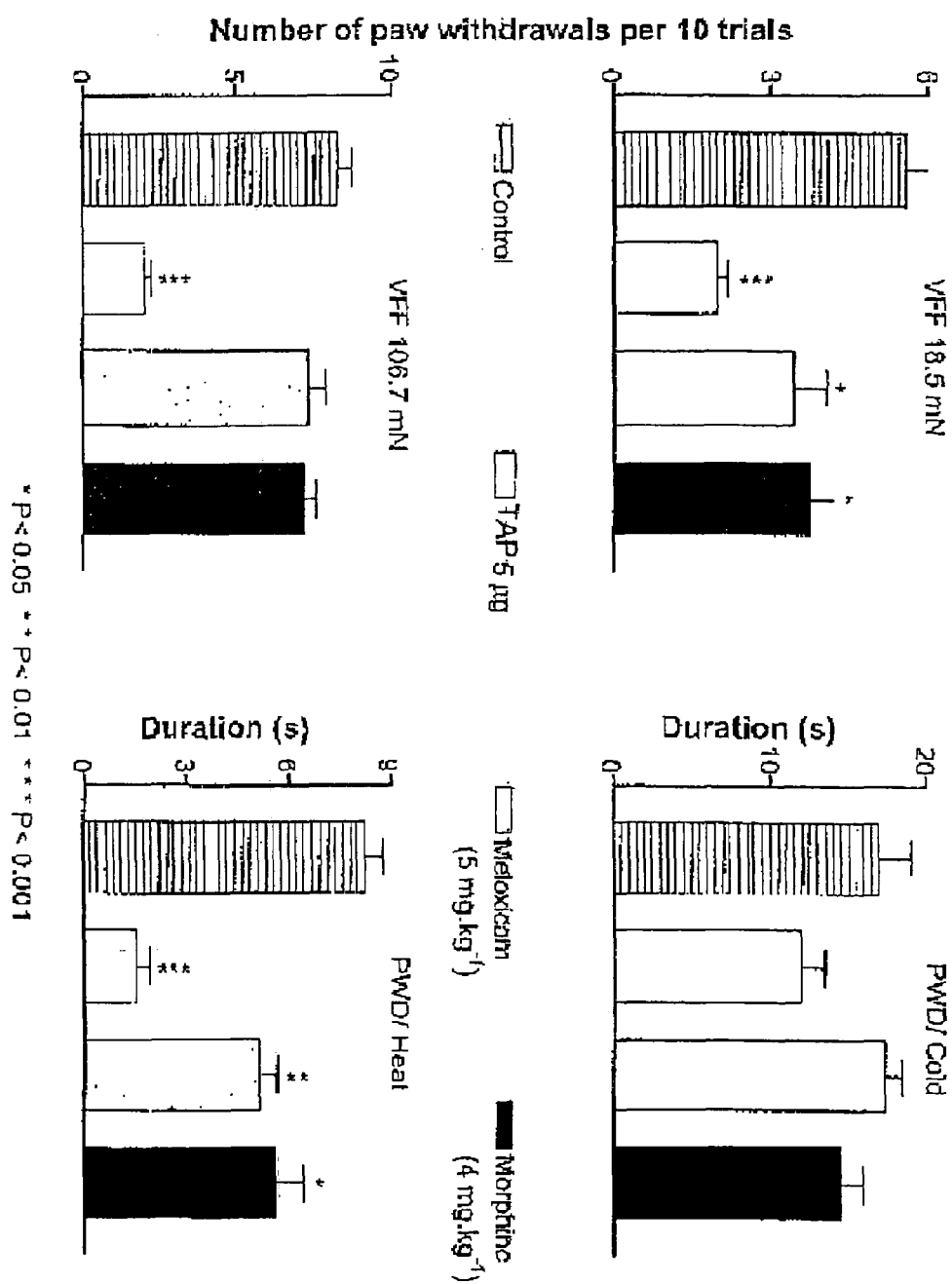
FIG. 10 represents the comparison of the different drugs for neuropathy.

The effects of treatment with TAP on the manifestations of neuropathy were compared to those observed with injections of either meloxican (5 mg/kg, i.p.) or morphine (4 mg/kg, i.p.) in two other groups of rats (n=6). Treatment with TAP induces a greater reduction of tactile allodynia and of thermal hyperalgesia that that observed with the two other drugs and this and a much lower dose. FIG. 10 represents this comparison. Each drug is administered by injection to a different group (n=6) of rats subjected to a neuropathy induced by SNI. All of the measurements were done at the peak of activity of each drug (45-60 minutes after the injection). The controls corresponding to the measures done on the rats subjected to a neuropathy prior to any treatment.

Figure 8:
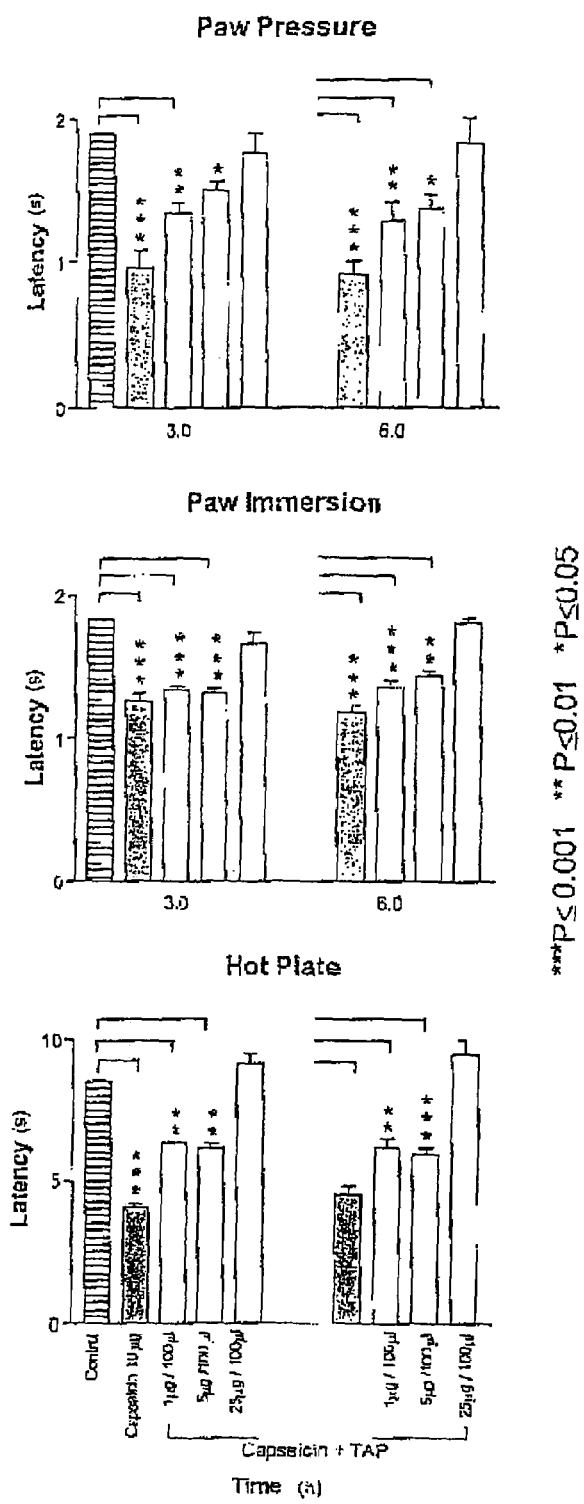
FIG. 8 represents a dose study of the peptides according to the invention in rats having hyperalgesia induced by the injection of capsaicin (somatic neurogenic pain)

Effects of Treatment with TAP on Hyperalgesia Induced by the Injection i.pl. of Capsaicin Intra-plantar injection of capsaicin (10 µg in 50 µl) resulted in a significant reduction of the latency times (hyperalgesia) observed at the time of the different pain tests. This reduction was maximum at the end of three to six hours and disappeared 24 hours after injection (Saade N. E., Massaad C. A., Ochoa-Chaar C. I., Atweh S. F., Safieh-Garabedian B., Jabbur S. J. 2000. *Possible contribution of neuropeptides and histamine to the hyperalgesia induced by intraplantar injection of capsaicin.* Eur. J. Neurosci. Abst. (suppl 11, Vol. 12: 123). Different groups of rats (n=5 rats in each group) were injected either with capsaicin or TAP (i.p.) then the capsaicin at the end of thirty minutes at doses of 1.5 or 25 µg/rat. The previous treatment with TAP resulted in a dose-dependent attenuation of the hyperalgesia induced by the capsaicin (FIG. 8). The more elevated dose, the injection of TAP involved a complete prevention of the hyperalgesia induced by the capsaicin. Injection of a dose of 25 µg of TAP did not result in significant modification of the latency times observed at the time of the different pain tests (FIG. 8, controls).

Effects of the Injection of TAP on Visceral Pain Induced by Capsaicin

Figure 9:
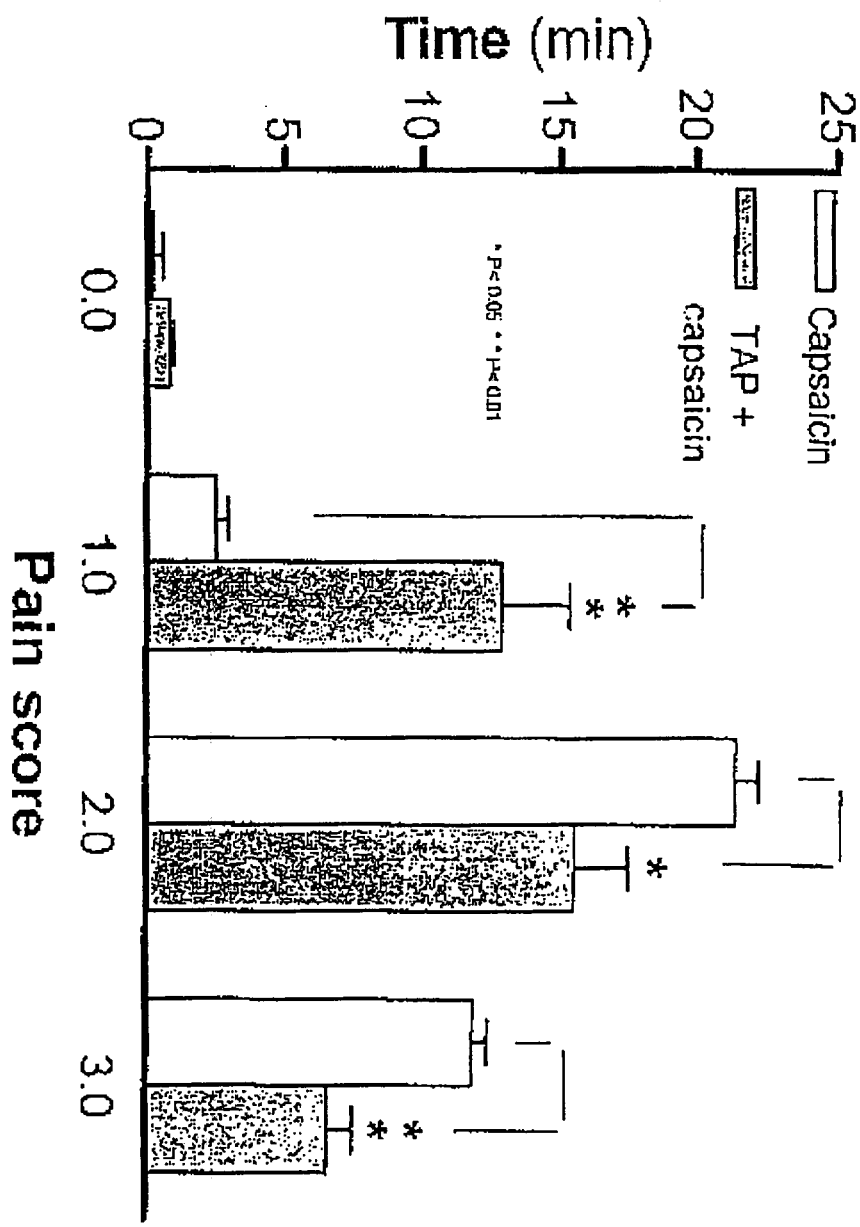
FIG. 9 represents the attenuation by the peptides according to the invention of the visceral pain induced by an intraperitoneal injection of capsaicin (visceral spasmodic neurogenic pain)

Rats (n=6) having received an injection i.p. of capsaicin (20 µg in 100 µl) had a response corresponding to level 0 over 0.2±0.3 minutes, level 1 over 2.51±0.45 minutes, level 2 over 21.5±0.8 minutes and level 3 over 11.84±0.43 minutes over a total observation period of 36 minutes (FIG. 9).

In another group of rats (n=6), injection of TAP (50 µg in 200 µl/rat) prior to injection of capsaicin (20 µg, i.p.), the following scores resulted: 0.82±0.18 minutes corresponding to level 0, 12.89±2.5 minutes corresponding to level 1, 15.62±0.9 minutes corresponding to level 2 and 6.67±0.09 minutes corresponding to level 3. Accordingly, prior treatment with TAP resulted in a significant shift to the left of the nociception scores induced by capsaicin (FIG. 9).

Example 3

Utilization of TAP for Manufacturing an Injectable Solution

TAP: 0.05 mg

Sterile, pyrogen-free distilled water 1.0 ml.

Sterilization by filtration, packaging in ampoules, bottles or multiple dose bottles.

Possible routes of administration are intraperitoneal, subcutaneous, intracerebral, intramuscular and intradermal injection.

---

The invention claimed is:

1. A method for treating pain, wherein said method comprises administering to a patient in need of said pain treatment an effective amount of a composition comprising at least one immune-system-inactive thymulin peptide analogue, wherein said analogue does not contain zinc, and wherein said peptide analogue is Glu-Ala-Lys-Ser-Gln-Gly-Gly-Ser-Asp (SEQ ID NO: 19) and wherein said composition is administered in an amount between 1 µg/kg and 10 mg/kg.

2. The method according to claim 1, wherein said composition further comprises a medicine having analgesic properties and/or anti-inflammatory properties.

3. The method according to claim 1, wherein said pain is at selected from the group consisting of: a migraine, sciatica, neuropathy and inflammatory pain.

4. The method according to claim 1, wherein said composition is administered parenterally or nasally.

* * * * *

SEQUENCE LISTING

```
<160> NUMBER OF SEQ ID NOS: 50

<210> SEQ ID NO 1
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: PyroGlu

<400> SEQUENCE: 1

Glu Ala Lys Ser Gln Gly Gly Ser Asp
 1               5
```

```
<210> SEQ ID NO 2
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: PyroGlu

<400> SEQUENCE: 2

Glu Ala Lys Ala Gln Gly Gly Ser Asn
 1               5

<210> SEQ ID NO 3
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: PyroGlu

<400> SEQUENCE: 3

Glu Ala Lys Ser Gln Gly Gly Ser Gln
 1               5

<210> SEQ ID NO 4
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: PyroGlu
<220> FEATURE:
<221> NAME/KEY: MOD_RES
<222> LOCATION: (9)
<223> OTHER INFORMATION: Beta-Ala
<220> FEATURE:
<223> OTHER INFORMATION: C-term amidated

<400> SEQUENCE: 4

Glu Ala Lys Ser Gln Gly Gly Ser Ala
 1               5

<210> SEQ ID NO 5
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: PyroGlu
<220> FEATURE:
<221> NAME/KEY: MOD_RES
<222> LOCATION: (9)
<223> OTHER INFORMATION: D-Asn

<400> SEQUENCE: 5
```

```
Glu Ala Lys Ser Gln Gly Gly Ser Asn
  1               5
```

<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: PyroGlu
<220> FEATURE:
<223> OTHER INFORMATION: C-term amidated

<400> SEQUENCE: 6

```
Glu Ala Lys Ser Gln Gly Gly Ser Asn
  1               5
```

<210> SEQ ID NO 7
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: PyroGlu

<400> SEQUENCE: 7

```
Glu Ala Lys Ser Asn Gly Gly Ser Asn
  1               5
```

<210> SEQ ID NO 8
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: PyroGlu
<220> FEATURE:
<221> NAME/KEY: MOD_RES
<222> LOCATION: (5)
<223> OTHER INFORMATION: Nva

<400> SEQUENCE: 8

```
Glu Ala Lys Ser Xaa Gly Gly Ser Asn
  1               5
```

<210> SEQ ID NO 9
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: PyroGlu

<400> SEQUENCE: 9

```
Glu Ala Lys Ser Gln Gly Gly Ala Asp
```

```
<210> SEQ ID NO 10
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Gln Ala Lys Ser Gln Gly Gly Ser Asp
 1               5

<210> SEQ ID NO 11
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Gln Ala Lys Ala Gln Gly Gly Ser Asn
 1               5

<210> SEQ ID NO 12
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Gln Ala Lys Ser Gln Gly Gly Ser Gln
 1               5

<210> SEQ ID NO 13
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)
<223> OTHER INFORMATION: Beta-Ala
<220> FEATURE:
<223> OTHER INFORMATION: C-term amidated

<400> SEQUENCE: 13

Gln Ala Lys Ser Gln Gly Gly Ser Ala
 1               5

<210> SEQ ID NO 14
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)
<223> OTHER INFORMATION: D-Asn

<400> SEQUENCE: 14
```

```
Gln Ala Lys Ser Gln Gly Gly Ser Asn
 1               5

<210> SEQ ID NO 15
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 15

Gln Ala Lys Ser Gln Gly Gly Ser Asn
 1               5

<210> SEQ ID NO 16
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Gln Ala Lys Ser Asn Gly Gly Ser Asn
 1               5

<210> SEQ ID NO 17
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)
<223> OTHER INFORMATION: Nva

<400> SEQUENCE: 17

Gln Ala Lys Ser Xaa Gly Gly Ser Asn
 1               5

<210> SEQ ID NO 18
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Gln Ala Lys Ser Gln Gly Gly Ala Asp
 1               5

<210> SEQ ID NO 19
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Glu Ala Lys Ser Gln Gly Gly Ser Asp
 1               5
```

```
<210> SEQ ID NO 20
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Glu Ala Lys Ala Gln Gly Gly Ser Asn
 1               5

<210> SEQ ID NO 21
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Glu Ala Lys Ser Gln Gly Gly Ser Gln
 1               5

<210> SEQ ID NO 22
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)
<223> OTHER INFORMATION: Beta-Ala
<220> FEATURE:
<223> OTHER INFORMATION: C-term amidated

<400> SEQUENCE: 22

Glu Ala Lys Ser Gln Gly Gly Ser Ala
 1               5

<210> SEQ ID NO 23
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)
<223> OTHER INFORMATION: D-Asn

<400> SEQUENCE: 23

Glu Ala Lys Ser Gln Gly Gly Ser Asn
 1               5

<210> SEQ ID NO 24
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 24
```

Glu Ala Lys Ser Gln Gly Gly Ser Asn
1               5

<210> SEQ ID NO 25
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Glu Ala Lys Ser Asn Gly Gly Ser Asn
1               5

<210> SEQ ID NO 26
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)
<223> OTHER INFORMATION: Nva

<400> SEQUENCE: 26

Glu Ala Lys Ser Xaa Gly Gly Ser Asn
1               5

<210> SEQ ID NO 27
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Glu Ala Lys Ser Gln Gly Gly Ala Asp
1               5

<210> SEQ ID NO 28
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Ala Lys Ser Gln Gly Gly Ser Asp
1               5

<210> SEQ ID NO 29
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Ala Lys Ala Gln Gly Gly Ser Asn
1               5

<210> SEQ ID NO 30

```
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Ala Lys Ser Gln Gly Gly Ser Gln
 1               5

<210> SEQ ID NO 31
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)
<223> OTHER INFORMATION: Beta-Ala
<220> FEATURE:
<223> OTHER INFORMATION: C-term amidated

<400> SEQUENCE: 31

Ala Lys Ser Gln Gly Gly Ser Ala
 1               5

<210> SEQ ID NO 32
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)
<223> OTHER INFORMATION: D-Asn

<400> SEQUENCE: 32

Ala Lys Ser Gln Gly Gly Ser Asn
 1               5

<210> SEQ ID NO 33
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 33

Ala Lys Ser Gln Gly Gly Ser Asn
 1               5

<210> SEQ ID NO 34
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Ala Lys Ser Asn Gly Gly Ser Asn
 1               5
```

```
<210> SEQ ID NO 35
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)
<223> OTHER INFORMATION: Nva

<400> SEQUENCE: 35

Ala Lys Ser Xaa Gly Gly Ser Asn
 1               5

<210> SEQ ID NO 36
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Ala Lys Ser Gln Gly Gly Ala Asp
 1               5

<210> SEQ ID NO 37
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Lys Ser Gln Gly Gly Ser Asp
 1               5

<210> SEQ ID NO 38
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Lys Ala Gln Gly Gly Ser Asn
 1               5

<210> SEQ ID NO 39
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Lys Ser Gln Gly Gly Ser Gln
 1               5

<210> SEQ ID NO 40
<211> LENGTH: 7
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)
<223> OTHER INFORMATION: Beta-Ala
<220> FEATURE:
<223> OTHER INFORMATION: C-term amidated

<400> SEQUENCE: 40

Lys Ser Gln Gly Gly Ser Ala
 1               5

<210> SEQ ID NO 41
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)
<223> OTHER INFORMATION: D-Asn

<400> SEQUENCE: 41

Lys Ser Gln Gly Gly Ser Asn
 1               5

<210> SEQ ID NO 42
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 42

Lys Ser Gln Gly Gly Ser Asn
 1               5

<210> SEQ ID NO 43
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Lys Ser Asn Gly Gly Ser Asn
 1               5

<210> SEQ ID NO 44
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: Nva

<400> SEQUENCE: 44
```

```
Lys Ser Xaa Gly Gly Ser Asn
  1               5
```

<210> SEQ ID NO 45
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

```
Lys Ser Gln Gly Gly Ala Asp
  1               5
```

<210> SEQ ID NO 46
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: PyroGlu

<400> SEQUENCE: 46

```
Glu Ala Lys Ser Gln Gly Gly Ser Asn
  1               5
```

<210> SEQ ID NO 47
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(4)
<223> OTHER INFORMATION: This region may encompass Ser, Lys-Ser,
      Ala-Lys-Ser, Glu-Ala-Lys-Ser, Gln-Ala-Lys-Ser,
      PyroGlu-Ala-Lys-Ser; see specification for
      detailed description of preferred embodiments

<400> SEQUENCE: 47

```
Xaa Xaa Xaa Xaa Gln Gly Gly Ser Asn
  1               5
```

<210> SEQ ID NO 48
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

```
Glu Ala Lys Ser
  1
```

<210> SEQ ID NO 49
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 49

Gln Ala Lys Ser
 1

<210> SEQ ID NO 50
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: PyroGlu

<400> SEQUENCE: 50

Glu Ala Lys Ser
 1
```